(12) United States Patent
Lin et al.

(10) Patent No.: US 8,275,594 B2
(45) Date of Patent: Sep. 25, 2012

(54) ENGINEERED SCAFFOLDS FOR INTERVERTEBRAL DISC REPAIR AND REGENERATION AND FOR ARTICULATING JOINT REPAIR AND REGENERATION

(75) Inventors: Chia-Ying Lin, Ann Arbor, MI (US); Frank LaMarca, Ann Arbor, MI (US); Stephen E. Feinberg, Ann Arbor, MI (US); William L. Murphy, Madison, WI (US); James R. Adox, Ann Arbor, MI (US); Scott J. Hollister, Saline, MI (US)

(73) Assignees: The Regents of the University of Michigan, Ann Arbor, MI (US); Wisconsin Alumni Research Foundation, Madison, WI (US)

( * ) Notice: Subject to any disclaimer, the term of this patent is extended or adjusted under 35 U.S.C. 154(b) by 1013 days.

(21) Appl. No.: 11/927,281

(22) Filed: Oct. 29, 2007

(65) Prior Publication Data

US 2008/0195211 A1    Aug. 14, 2008

Related U.S. Application Data

(60) Provisional application No. 60/855,234, filed on Oct. 30, 2006.

(51) Int. Cl.
*G06G 7/58* (2006.01)
(52) U.S. Cl. .......................................... 703/11
(58) Field of Classification Search ...................... 703/11
See application file for complete search history.

(56) References Cited

U.S. PATENT DOCUMENTS

| | | | |
|---|---|---|---|
| 4,355,429 A | 10/1982 | Mittelmeier et al. | |
| 4,778,473 A | 10/1988 | Matthews et al. | |
| 4,911,718 A | 3/1990 | Lee et al. | |
| 5,071,437 A | 12/1991 | Steffee | |
| 5,258,043 A * | 11/1993 | Stone ........................... | 264/108 |
| 5,609,641 A * | 3/1997 | Johnson et al. ............ | 623/20.32 |
| 5,972,032 A | 10/1999 | Lopez et al. | |
| 5,984,967 A | 11/1999 | Zdeblick et al. | |
| 6,090,143 A | 7/2000 | Meriwether et al. | |
| 6,231,615 B1 | 5/2001 | Preissman | |
| 6,264,695 B1 | 7/2001 | Stoy | |
| 6,309,420 B1 | 10/2001 | Preissman | |
| 6,541,022 B1 | 4/2003 | Murphy et al. | |
| 6,582,467 B1 | 6/2003 | Teitelbaum et al. | |
| 6,613,091 B1 | 9/2003 | Zdeblick et al. | |
| 6,767,928 B1 | 7/2004 | Murphy et al. | |
| 7,004,971 B2 | 2/2006 | Serhan et al. | |
| 7,008,452 B2 | 3/2006 | Hawkins | |
| 7,083,624 B2 | 8/2006 | Irving | |
| 7,087,200 B2 | 8/2006 | Taboas et al. | |
| 7,112,222 B2 | 9/2006 | Fraser et al. | |
| 7,112,417 B2 | 9/2006 | Vyakarnam et al. | |
| 7,166,570 B2 | 1/2007 | Hunter et al. | |
| 7,174,282 B2 | 2/2007 | Hollister et al. | |
| 2002/0026244 A1 | 2/2002 | Trieu | |
| 2003/0006534 A1 | 1/2003 | Taboas et al. | |
| 2003/0069718 A1 | 4/2003 | Hollister et al. | |
| 2003/0074096 A1 | 4/2003 | Das et al. | |
| 2004/0034428 A1 | 2/2004 | McKay | |
| 2005/0043816 A1 * | 2/2005 | Datta et al. .................. | 623/23.61 |
| 2005/0055099 A1 | 3/2005 | Ku | |
| 2006/0141623 A1 * | 6/2006 | Smith et al. .................. | 435/383 |
| 2006/0276925 A1 | 12/2006 | Lin et al. | |

OTHER PUBLICATIONS

Sun et al., "Bio-CAD Modeling and Its Applications in Computer-Aided Tissue Engineering," Computer-Aided Design (Sep. 15, 2005) vol. 37, pp. 1097-1114.*

* cited by examiner

*Primary Examiner* — Jerry Lin
(74) *Attorney, Agent, or Firm* — Quarles & Brady LLP

(57) ABSTRACT

Methods for the engineering and preparation of intervertebral disc repair scaffolds and articulating joint repair scaffolds are disclosed. The methodology utilizes either magnetic resonance images or combined magnetic resonance and computed tomography images as a template for creating either the intervertebral scaffold or the joint repair scaffold (e.g., osteochondral scaffold) with fixation to the underlying bone. The disc scaffold design may include an outer annulus that may contain desired structures and a central nucleus pulposus region that could either contain a designed microstructure or a contained hydrogel. The osteochondral scaffold may include a bone compartment interface with a cartilage compartment. The bone compartment may interface with a cutout portion of the bone through fixation components. Different microstructure designs may be created for the bone and cartilage compartment to represent desired mechanical and mass transport properties. The scaffolds are designed with a microstructure that controls elastic and permeability property distribution within the scaffold.

22 Claims, 10 Drawing Sheets

24

26

ENGINEERED SCAFFOLDS FOR INTERVERTEBRAL DISC REPAIR AND REGENERATION AND FOR ARTICULATING JOINT REPAIR AND REGENERATION

CROSS-REFERENCES TO RELATED APPLICATIONS

This application claims priority from U.S. Provisional Patent Application No. 60/855,234 filed Oct. 30, 2006.

STATEMENT REGARDING FEDERALLY SPONSORED RESEARCH

This invention was made with government support under grant number R01 DE 13608 and grant number AR 052893 awarded by the National Institutes of Health. The government has certain rights in the invention.

BACKGROUND OF THE INVENTION

1. Field of the Invention

This invention relates to biomaterial scaffolds, and more particularly to biomaterial scaffolds for intervertebral disc repair and/or regeneration and biomaterial scaffolds for articulating joint repair and/or regeneration.

2. Description of the Related Art

It is reported in U.S. Patent Application Publication No. 2003/0069718 and corresponding U.S. Pat. No. 7,174,282 that biomaterial scaffolds for tissue engineering perform three primary functions. The first is to provide a temporary function (stiffness, strength, diffusion, and permeability) in tissue defects. The second is to provide a sufficient connected porosity to enhance biofactor delivery, cell migration and regeneration of connected tissue. The third requirement is to guide tissue regeneration into an anatomic shape. It is further noted that the first two functions present conflicting design requirements. Specifically, increasing connected porosity to enhance cell migration and tissue regeneration decreases mechanical stiffness and strength, whereas decreasing porosity increases mechanical stiffness and strength but impedes cell migration and tissue regeneration.

U.S. 2003/0069718 provides a design methodology for creating biomaterial scaffolds with internal porous architectures that meet the need for mechanical stiffness and strength and the need for connected porosity for cell migration and tissue regeneration. The design methods of U.S. 2003/0069718 combine image-based design of pore structures with homogenization theory to compute effective physical property dependence on material microstructure. Optimization techniques are then used to compute the optimal pore geometry. The final optimized scaffold geometry voxel topology is then combined with a voxel data set describing the three dimensional anatomic scaffold shape which may be obtained by magnetic resonance (MR) images or combined MR and computed tomography (CT) images. Density variations within the anatomic scaffold voxel database are used as a map to guide where different optimized scaffold voxel topologies are substituted. The final voxel representation of the anatomically shaped scaffold with optimized interior architecture is then converted automatically by software into either a surface representation or wire frame representation for fabrication of the scaffold by way of solid free form fabrication or casting.

While the advances of U.S. 2003/0069718 have significantly improved the design of biomaterial scaffolds for tissue engineering, there is still a need for further advances in this technology to provide for even more optimized biomaterial scaffolding and tissue generation systems.

SUMMARY OF THE INVENTION

The present invention provides methods for the engineering and preparation of scaffolding and tissue generation systems for the repair of bone/cartilage composites, including, but not limited to, osteochondral scaffolds/tissue repair systems for the tibial plateau, proximal femoral head, acetabulum, humeral head, and intervertebral spinal disc repair and regeneration. The methodology utilizes either magnetic resonance images or combined magnetic resonance and computed tomography images as a template for creating either the intervertebral scaffold as well as the fixation for the scaffolding into adjacent vertebral bodies or the osteochondral scaffold with fixation to the underlying bone.

The disc scaffold design may include an outer annulus that may contain desired porous structures and a central nucleus pulposus region that could either contain a designed porous microstructure or a contained hydrogel or other bioactive agent(s). Instrumentation for surgical placement is also included. The scaffolding has designed microstructure that controls elastic and permeability property distribution within the intervertebral zone.

The osteochondral scaffold may include a bone compartment interface with a cartilage compartment. The bone compartment may interface with a cutout portion of the bone through fixation components such as pegs and screws and the like. Different microstructure designs may be created for the bone and cartilage compartment to represent desired mechanical and mass transport properties.

Advantages of the method of the invention include the ability to create designed microstructures that can mimic intervertebral load carrying capability, to provide directed nutrients to seeded/migrated cells in the disc, and the capability of creating disc structures that can regrow natural tissue. This provides a potential advantage over artificial discs, which as synthetic materials are subject to wear and fatigue failure. Regrowth of a new disc would provide a natural tissue that could remodel in response to applied loads and would be subject to the wear and fatigue problems of synthetic materials. In addition, the capability of creating designed scaffolding would provide the necessary load bearing capability via designed elasticity and permeability for tissue engineering an intervertebral disc that non-designed scaffolds could not provide. In addition, if the designed scaffolding is used for fusion, it could provide load bearing capability that would eliminate the need for some or all of the hardware needed for current interbody fusion techniques.

For the osteochondral scaffold, advantages include the ability to design a separate bone/cartilage interface, and more importantly, the ability to design these bone and cartilage compartments to have desired effective mechanical and mass transport properties. In addition, the osteochondral scaffolds could have virtually any interface with surrounding tissue or for surgical fixation.

For the total joint interface, advantages again include the ability to have control over the designed microstructure interface, giving it desired interface elasticity properties and the ability to control geometric thickness.

In one aspect of the invention, there is provided a method for designing a tissue scaffold for generating tissue in a patient. In the method, a first set of databases is created representing a plurality of porous microstructure designs for the scaffold in image based format. A second database is created representing scaffold exterior geometry desired to replace the native tissue in the patient in image based format. A third database is created representing scaffold external fixation structure. Then, the first set of databases representing the desired microstructure designs and the second database and the third database are merged into an image-based design of the scaffold. The image-based design may then be converted to a fabrication geometry such as surface representation or wireframe representation.

In one form, the scaffold external fixation structure is designed to be porous, and is designed to include at least one projection extending away from the scaffold. Example projections are a peg or a spike or a plate. The projection can be designed to include fastening means selected from threads and/or throughholes. In one embodiment, the scaffold is designed for intervertebral disc repair. In another embodiment, the scaffold is designed for articulating joint repair. In yet another embodiment, the scaffold is designed for total joint replacement.

The scaffold external fixation structure can be designed to include at least one projection extending away from the scaffold, and at least one marking including a tracer that provides enhanced visibility via a medical imaging device can be placed on the at least one projection. The scaffold external fixation structure can be designed to include at least one projection extending away from the scaffold, and at least one radiopaque marking that provides enhanced visibility via a fluoroscope can be placed on the at least one projection. The scaffold can be designed to include a region of no material or radiolucent material such that the region forms an imaging window for enhanced visibility through the imaging window via a medical imaging device. The scaffold external fixation structure can be designed to include at least one projection extending away from the scaffold, and at least one marking for alignment during implantation can be placed on the at least one projection.

In another aspect of the invention, there is provided a method for designing an intervertebral disc scaffold. In the method, a first set of databases is created representing a plurality of porous microstructure designs for the scaffold in image based format. A second database is created representing scaffold exterior geometry desired to replace the native disc in the patient in image based format. Then, the first set of databases representing the desired microstructure designs are merged with the second database into an image-based design of the scaffold. The image-based design can be converted to a fabrication geometry. The second database can represent an intervertebral space to be occupied by the scaffold.

In one form, the image-based design of the scaffold can be designed to include an outer annulus having a first designed porous microstructure, and the image-based design of the scaffold can be designed to include a central region having a second designed microstructure. In another form, the image-based design of the scaffold can be designed to include an outer annulus having a first designed porous microstructure, and the image-based design of the scaffold can be designed to include a central region designed for containing a biocompatible material. At least one of the microstructure designs can be a wavy fiber design. In one form, the image-based design of the scaffold is designed to include spherical or elliptical pores.

The scaffold can be designed to include at least one projection, such as a plate, peg or spike, extending away from the scaffold, and at least one marking including a tracer that provides enhanced visibility via a medical imaging device can be placed on the at least one projection. The scaffold can be designed to include at least one projection extending away from the scaffold, and at least one radiopaque marking that provides enhanced visibility via a fluoroscope can be placed on the at least one projection. The scaffold can be designed to include at least one projection extending away from the scaffold, and at least one marking for alignment during implantation can be placed on the at least one projection. The scaffold can be designed to include a region of no material or radiolucent material such that the region forms an imaging window for enhanced visibility through the imaging window via a medical imaging device.

In yet another aspect of the invention, there is provided a method for designing an osteochondral scaffold for replacing native tissue in a patient. In the method, a first set of databases is created representing a plurality of porous microstructure designs for the scaffold in image based format. A second database is created representing scaffold exterior geometry desired to replace the native tissue in the patient in image based format. The first set of databases representing the desired microstructure designs are merged with the second database into an image-based design of the scaffold that includes a bone region designed to have a first physical or biochemical property and a cartilage region designed to have a second physical or biochemical property. At least one of the microstructure designs can be a wavy fiber design. The bone region can be designed to have a pore structure different from a pore structure of the cartilage region. The cartilage region can be designed to include spherical or elliptical pores. The bone region can be designed to allow greater mass transport than the cartilage region.

The first physical or biochemical property can be a mechanical property (such as elasticity), and the second physical or biochemical property can be a mechanical property (such as elasticity). The first physical or biochemical property can be a mass transport property (such as permeability), and the second physical or biochemical property can be a mass transport property (such as permeability). The first physical or biochemical property can be a biochemical property (such as bioactive agent delivery control), and the second physical or biochemical property can be a biochemical property (such as bioactive agent delivery control).

In one embodiment, the first physical or biochemical property can be achieved by coating at least a portion of the bone region with an osteoconductive mineral. In another embodiment, the first physical or biochemical property can be achieved by coating at least a portion of the bone region with an osteoconductive mineral comprising a calcium compound. In yet another embodiment, the first physical or biochemical property can be achieved by coating at least a portion of the bone region with an osteoconductive mineral comprising a material selected from hydroxyapatite, calcium-deficient carbonate-containing hydroxyapatite, tricalcium phosphate, octacalcium phosphate, dicalcium phosphate, calcium phosphate, and mixtures thereof. In still another embodiment, the first physical or biochemical property can be achieved by coating at least a portion of the bone region with an osteoconductive mineral comprising a plurality of discrete mineral islands. In yet another embodiment, the first physical or biochemical property can be achieved by coating at least a portion of the bone region with an osteoconductive mineral comprising a substantially homogeneous mineral coating. In still another embodiment, the first physical or biochemical property can be achieved by coating at least a portion of the bone region with an osteoconductive mineral and associating a bioactive agent with the mineral coating. The bioactive agent can be selected from bone morphogenetic proteins.

In yet another aspect of the invention, there is provided a method for designing a joint replacement for a patient. In the method, a first set of databases is created representing a plurality of porous microstructure designs for the joint replacement in image based format. A second database is created representing joint replacement exterior geometry in image based format. The first set of databases representing the desired microstructure designs are merged with the second database into an image-based design of the joint replacement that includes a bone region designed to have a first physical or biochemical property and a surface region designed to have a second physical or biochemical property. At least one of the microstructure designs can be a wavy fiber design. The bone region can be designed to have a pore structure different from a pore structure of the surface region. The surface region can be designed to include spherical or elliptical pores. The bone region can be designed to allow greater mass transport than the cartilage region.

The first physical or biochemical property can be a mechanical property (such as elasticity), and the second physical or biochemical property can be a mechanical property (such as elasticity). The first physical or biochemical property can be a mass transport property (such as permeability), and the second physical or biochemical property can be a mass transport property (such as permeability). The first physical or biochemical property can be a biochemical property (such as bioactive agent delivery control), and the second physical or biochemical property can be a biochemical property (such as bioactive agent delivery control).

In one embodiment, the first physical or biochemical property can be achieved by coating at least a portion of the bone region with an osteoconductive mineral. In another embodiment, the first physical or biochemical property can be achieved by coating at least a portion of the bone region with an osteoconductive mineral comprising a calcium compound. In yet another embodiment, the first physical or biochemical property can be achieved by coating at least a portion of the bone region with an osteoconductive mineral comprising a material selected from hydroxyapatite, calcium-deficient carbonate-containing hydroxyapatite, tricalcium phosphate, octacalcium phosphate, dicalcium phosphate, calcium phosphate, and mixtures thereof. In still another embodiment, the first physical or biochemical property can be achieved by coating at least a portion of the bone region with an osteoconductive mineral comprising a plurality of discrete mineral islands. In yet another embodiment, the first physical or biochemical property can be achieved by coating at least a portion of the bone region with an osteoconductive mineral comprising a substantially homogeneous mineral coating. In still another embodiment, the first physical or biochemical property can be achieved by coating at least a portion of the bone region with an osteoconductive mineral and associating a bioactive agent with the mineral coating. The bioactive agent can be selected from bone morphogenetic proteins.

In still another aspect of the invention, there is provided an intervertebral disc repair and/or regeneration scaffold. The scaffold includes a central core shaped to approximate the nucleus pulposus of a natural intervertebral disc wherein the central core has a first porous microstructure. The scaffold further includes an outer annulus shaped to approximate the annulus fibrosus of a natural intervertebral disc wherein the outer annulus is connected to and surrounds the central core and wherein the outer annulus has a second porous microstructure. In one embodiment, the central core and the outer annulus have different elasticity. In another embodiment, the central core and the outer annulus have different permeability. In yet another embodiment, the central core and the outer annulus have different bioactive agent release properties.

In one form, the central core includes a biocompatible material. In another form, the central core includes a hydrogel. In yet another form, the central core includes a bioactive agent. In one embodiment, the bioactive agent is selected from undifferentiated chondrocyte precursor cells from periosteum, mesenchymal stem cells from bone marrow, chondrocytes, sclerosing agents, angiogenesis activators, angiogenesis inhibitors, and mixtures thereof. The central core can comprise wavy fibers.

The scaffold can be formed from biodegradable polymers, biodegradable ceramics, non-biodegradable metals, non-biodegradable metal alloys, or mixtures thereof. The scaffold can include at least one marking including a tracer that provides enhanced visibility via a medical imaging device. The scaffold can include at least one radiopaque marking that provides enhanced visibility via a fluoroscope. The scaffold can include a region of no material or radiolucent material such that the region forms an imaging window for enhanced visibility through the imaging window via a medical imaging device. The scaffold can include at least one marking for alignment during implantation.

In one embodiment, an osteoconductive mineral coating is disposed on at least a portion of the scaffold. The osteoconductive mineral coating can include a plurality of discrete mineral islands. Alternatively, the osteoconductive mineral coating can include a substantially homogeneous mineral coating. The osteoconductive mineral coating can include a calcium compound. For example, the osteoconductive mineral coating can include hydroxyapatite, calcium-deficient carbonate-containing hydroxyapatite, tricalcium phosphate, octacalcium phosphate, dicalcium phosphate, calcium phosphate, and mixtures thereof. A bioactive agent can be associated with the mineral coating. Example bioactive agent are bone morphogenetic proteins.

These and other features, aspects, and advantages of the present invention will become better understood upon consideration of the following detailed description, drawings and appended claims.

BRIEF DESCRIPTION OF THE DRAWINGS

Like reference numerals will be used to refer to like or similar parts from Figure to Figure in the following description.

DETAILED DESCRIPTION OF THE INVENTION

An intervertebral disc scaffolding according to the invention includes: (i) a designed porous microstructured scaffolding itself, made from biodegradable polymers (e.g., polycaprolactone), biodegradable ceramics (e.g., calcium phosphate), or non-biodegradable metals or metal alloys (e.g., titanium or titanium alloys), or mixtures thereof, and (ii) fixation structures for integrating the designed intervertebral scaffolding to the adjacent vertebrae. As used herein, a "biodegradable" material is one which decomposes under normal in vivo physiological conditions into components which can be metabolized or excreted.

The scaffolding may include a bioactive agent at any desired location in the scaffold. A "bioactive agent" as used herein includes, without limitation, physiologically or pharmacologically active substances that act locally or systemically in the body. A bioactive agent is a substance used for the treatment, prevention, diagnosis, cure or mitigation of disease or illness, or a substance which affects the structure or function of the body or which becomes biologically active or more active after it has been placed in a predetermined physiological environment. Bioactive agents include, without limitation, cells, enzymes, organic catalysts, ribozymes, organometallics, proteins (e.g., bone morphogenetic proteins), demineralized bone matrix, bone marrow aspirate, undifferentiated chondrocyte precursor cells from periosteum, mesenchymal stem cells from bone marrow, chondrocytes, sclerosing agents, angiogenesis activators, angiogenesis inhibitors, glycoproteins, peptides, polyamino acids, antibodies, nucleic acids, steroidal molecules, antibiotics, antimycotics, cytokines, fibrin, collagen, fibronectin, vitronectin, hyaluronic acid, growth factors (e.g., transforming growth factors and fibroblast growth factor), carbohydrates, statins, oleophobics, lipids, extracellular matrix and/or its individual components, pharmaceuticals, and therapeutics.

In areas of the scaffold where bone growth is desired, preferred bioactive agents include, without limitation, bone morphogenetic proteins (such as rhBMP-2, BMP-2, BMP-4, BMP-7, BMP-14), demineralized bone matrix, bone marrow aspirate, growth and development factor-5 (GDF-5), or platelet rich plasma (PRP). In areas of the scaffold where cartilage or fibrous tissue growth is desired, preferred bioactive agents include, without limitation, undifferentiated chondrocyte precursor cells from periosteum, mesenchymal stem cells from bone marrow, chondrocytes, sclerosing agents (such as surfactants, polidocanol, and sodium morrhuate), angiogenesis activators, and angiogenesis inhibitors.

Figure 1:
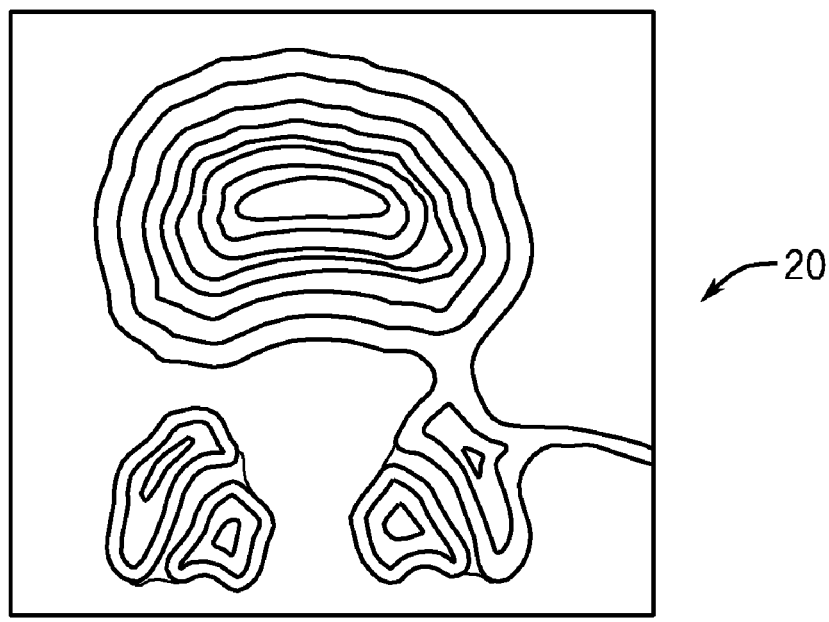
FIG. 1 shows a slice from an external shape design dataset for an intervertebral disc. The internal rings represent the different density regions for mapping heterogeneous microstructure.

The starting point for creating the scaffold may be either a CT image MR image, a combined MR/CT image, or a digitized cadaver vertebral image. The resulting images provide the external shape and design space for the disc scaffolding and fixation. These images are stored as density distribution within a voxel dataset. In addition, the tissue density distribution from the images provides a flag for placing the designed microstructure within the global design space. In addition, the global density distribution used as a mapping flag may also be created using global topology optimization. An example of a global density distribution of a cross-sectional intervertebral disc image 20 is shown in FIG. 1 wherein the internal rings mark the different density regions for mapping heterogeneous microstructure.

A porous microstructure design may be created using the image based design methods described in U.S. Patent Application Publication No. 2003/0069718, which is incorporated herein by reference as if fully set forth herein. The steps for performing the scaffold optimization of the present invention using the image based design methods described in U.S. Patent Application Publication No. 2003/0069718 are as follows. In step 1, the methodology creates unit cell voxel databases. That is, a set of base unit cell architectures are created in voxel format ranging over all design parameters. In step 2, the method calculates effective physical properties. That is, the method solves homogenization equations for each unit cell to calculate effective physical property of the scaffold and the tissue that will grow into the scaffold pores. The method can also determine functional dependence of effective stiffness, permeability, and porosity on cell design parameters. In step 3, the method formulates and solves optimization algorithms of unit cell parameters. That is, the method solves the optimization problem that will find the best match of both scaffold and regenerate tissue properties to naturally occurring tissue properties. The solution gives the optimal design parameters for the unit cell architecture. In step 4, the method creates an anatomic shape voxel database. That is, the method creates a voxel database of the anatomic scaffold shape with different densities representing different scaffold architectures. In step 5, the method merges the anatomic and unit cell architecture data base. That is, the method uses image-based Boolean operations to merge the anatomic data base with density distribution with individual sets of unit cell databases. In step 6, the method converts the voxel design to a surface or wire frame geometry. That is, the method converts the resulting complete scaffold design in voxel format to either a triangular facet representation or a wire frame representation that can be used in solid free form systems. In step 7, the method fabricates the design scaffold from biomaterial using direct or indirect (casting) solid free form techniques.

Figure 2A:
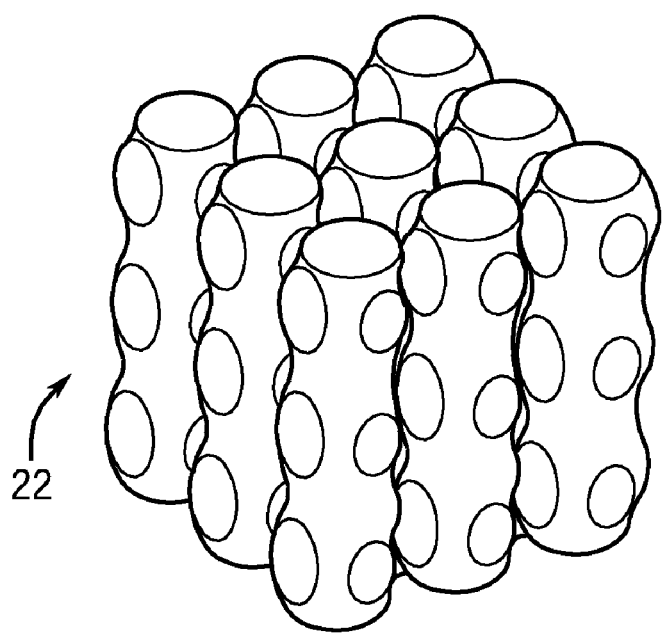
FIG. 2A shows an example of a designed microstructure for scaffolding with interconnected cylindrical pores.
Figure 2B:
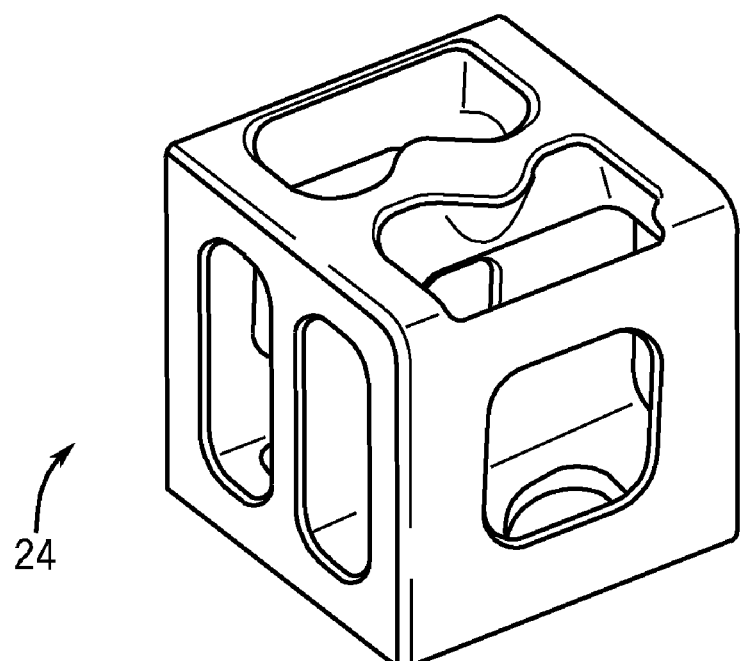
FIG. 2B shows an example of a designed microstructure for scaffolding with topology optimized microstructure.
Figure 2C:
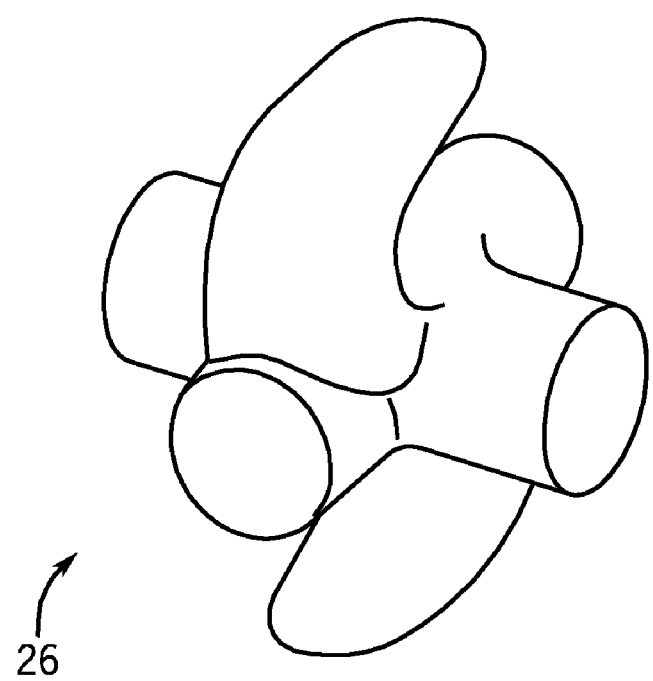
FIG. 2C shows an example of a designed microstructure for scaffolding with wavy fibered microstructure.

In the present invention, the scaffold microstructure will be created to provide a specified heterogeneous distribution of effective elastic and permeability properties, designed to provide load bearing capability similar to a natural human intervertebral disc, along with pathways for nutrient nutrition. The microstructure design may comprise, but is not limited to, the following: (1) an interconnected system of spherical pores with varying diameter; (2) an interconnected system of straight or curved struts with varying diameter; (3) topology optimized microstructures; or (4) wavy fibered structures. FIG. 2A shows an example of a designed microstructure 22 for scaffolding with interconnected cylindrical pores. FIG. 2B shows an example of a designed microstructure 24 for scaffolding with topology optimized microstructure. FIG. 2C shows an example of a designed microstructure 26 for scaffolding with wavy fibered microstructure.

In the microstructure design, the image-based methods as in U.S. 2003/0069718 can be used to design an internal architecture optimized to match target bone or cartilage Young's moduli. In particular, the modulus ranges for trabecular bone and intervertebral disc that we would target for fusion and disc repair are: Bone: 30-200 MPa, and Intervertebral Disc: 0.4-10 MPa.

Figure 3:
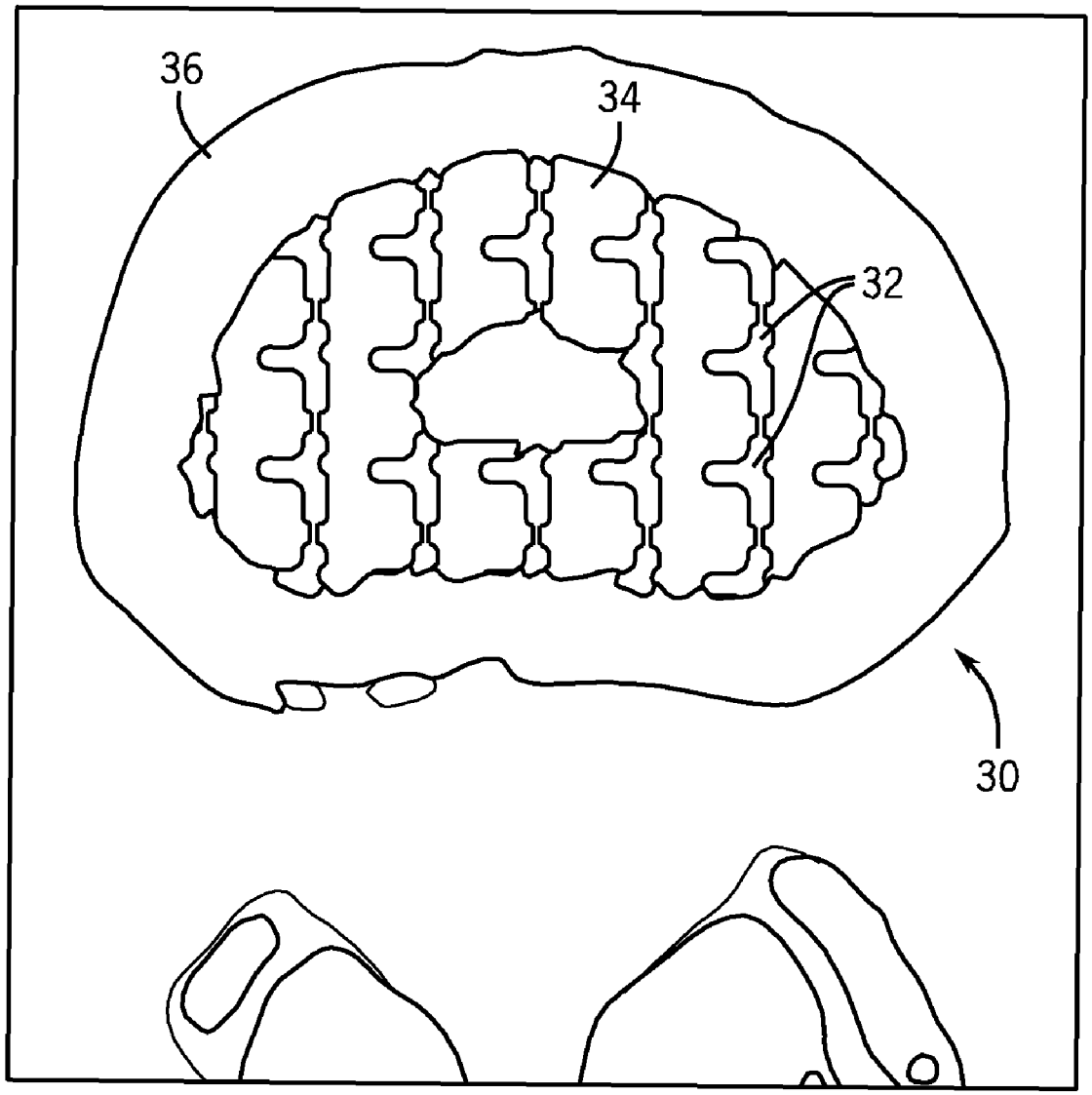
FIG. 3 shows a slice of a designed intervertebral scaffolding with wavy fibered microstructure in the correct anatomic shape. The central region approximates the shape of the nucleus pulposus in a natural intervertebral disc.

This microstructure may be created by repeating basic unit cell design blocks. These unit cell blocks are also represented as a density distribution within a structured voxel dataset. Once the unit cell designs and global shape template image databases are created, they are merged using image Boolean operations to create the final design porous microstructure scaffolding as described in U.S. Patent Application Publication No. 2003/0069718. A prototype for a designed intervertebral disc repair and/or regeneration scaffolding is shown in FIG. 3. FIG. 3 shows a cross section of a designed intervertebral scaffolding 30 with wavy fibered microstructure 32 in the correct anatomic shape. The central region 34 approximates the shape of the nucleus pulposus in a natural intervertebral disc. The outer region 36 approximates the shape of the outer annulus fibrosus in a natural intervertebral disc.

The next step in creating the scaffolding is to create a fixation structure for attaching the disk scaffolding to the adjacent vertebrae. This fixation structure is also created using the same combination of microstructure and global design datasets, as it may be porous to allow bone ingrowth. This fixation may take many forms. One example fixation is a plate attached directly to the scaffold disc. An example of this fixation is shown in the scaffold 40 of FIG. 4.

Figure 4:
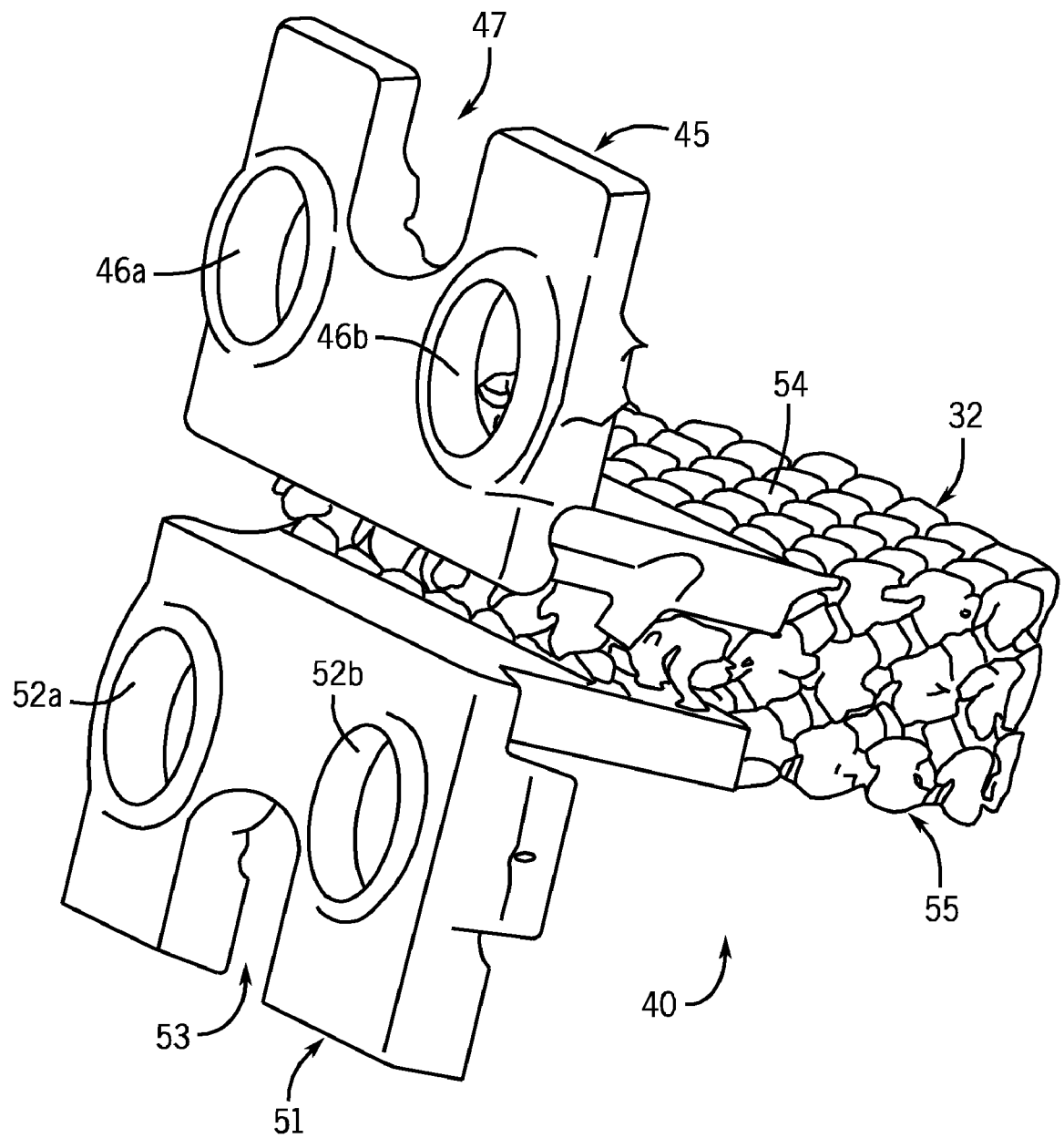
FIG. 4 shows an example of an integrated anterior plate fixation on a disc regeneration scaffold. This integrated plating can be used for either disc regeneration or spinal fusion.

In FIG. 4, the wavy fibered microstructure 32 is in the correct anatomic shape for a natural intervertebral disc. A top fixation plate 45 includes spaced apart fastener holes 46a, 46b and a top central U-shaped cutaway section 47. A bottom fixation plate 51 includes spaced apart fastener holes 52a, 52b, and a bottom central inverted U-shaped cutaway section 53. The wavy fibered microstructure 32 is integral with the fixation plates 45, 51. When used in intervertebral disc repair, the wavy fibered microstructure 32 of the scaffold 40 would be positioned in the intervertebral space created by removal of the intervertebral disc between adjacent vertebrae. Fasteners would be inserted in fastener holes 46a, 46b for anterior attachment to a first upper vertebra, and fasteners would be inserted in fastener holes 52a, 52b for anterior attachment to an adjacent second lower vertebra. The top end surface 54 of the wavy fibered microstructure 32 would contact a lower surface of the first upper vertebra, and the opposite bottom end surface 55 of the wavy fibered microstructure 32 would contact an upper surface of the second lower vertebra. The wavy fibered microstructure 32 thereby provides mechanical load bearing support between the first upper vertebra and the second lower vertebra.

The vertical dimensions of the wavy fibered microstructure 32 can be adjusted accordingly for various different intervertebral distances. Likewise, the horizontal length of the fixation plates 45, 51 and their spatial relationship can be varied to ensure proper location of the fastener holes 46a, 46b, 52a, 52b adjacent the first upper vertebra and the second lower vertebra for securing the scaffold 40 to the first upper vertebra and the second lower vertebra. By varying the dimensions of the wavy fibered microstructure 32 and the fixation plates 45, 51, different size scaffolds 40 can be provided for selection by a surgeon.

The scaffold 40 can comprise a porous biocompatible and biodegradable (if desired) porous material selected from polymeric materials, metallic materials, ceramic materials and mixtures thereof. In one example embodiment, the scaffold 40 is formed from polycaprolactone, a biocompatible and biodegradable polymer. However, other polymers such as polylactide, polyglycolide, poly(lactide-glycolide), poly (propylene fumarate), poly(caprolactone fumarate), polyethylene glycol, and poly(glycolide-co-caprolactone) may be advantageous for forming the scaffold 40. As used herein, a "biocompatible" material is one which stimulates only a mild, often transient, implantation response, as opposed to a severe or escalating response.

An osteoconductive mineral coating can formed on at least a portion of the scaffold 40 where bone growth is desired. The osteoconductive mineral coating can comprises a plurality of discrete mineral islands, or the mineral coating can be formed on the entire surface areas of the scaffold 40. In one example form, the osteoconductive mineral coating comprises a substantially homogeneous mineral coating. In one example embodiment, the mineral coatings may be any suitable coating material containing calcium and phosphate, such as hydroxyapatite, calcium-deficient carbonate-containing hydroxyapatite, tricalcium phosphate, amorphous calcium phosphate, octacalcium phosphate, dicalcium phosphate, calcium phosphate, and the like. The mineral coating may also include a plurality of layers having distinct dissolution profiles to control dissolution order, kinetics and bioactive delivery properties. Under physiological conditions, the solubility of calcium phosphate materials are as follows: amorphous calcium phosphate>dicalcium phosphate>octacalcium phosphate>tricalcium phosphate>hydroxyapatite. Thus, a plurality of various calcium phosphate layers can provide a broad range of dissolution patterns. Incorporation of blank layers (i.e., calcium phosphate layers not containing any bioactive agent) can provide for delayed release. Also, the incorporation of layers having different concentrations of bioactive agent can provide for varying release rates.

A bioactive agent can be associated with uncoated biocompatible material forming the scaffold 40 and/or the mineral coated portions of the scaffold 40. Different release rates of the bioactive agent would be possible from uncoated and coated areas of the scaffold 40. While various bioactive agents listed above are suitable for use with the scaffold 40, in one example embodiment, the bioactive agent is selected from bone morphogenetic proteins, demineralized bone matrix, bone marrow aspirate, and mixtures thereof. Bone morphogenetic proteins have been shown to be excellent at growing bone and powdered recombinant human BMP-2 is available in certain commercial products. Demineralized bone matrix includes osteoinductive proteins (e.g., bone morphogenetic proteins), and can be used in a particle or fiber form. Bone marrow aspirate contains osteoprogenitor cells, and the patient's bone marrow can be readily harvested with a needle. As used herein, a bioactive agent is "associated" with the polymer and/or the coating if the bioactive agent is directly or indirectly, physically or chemically bound to the polymer and/or the coating. A bioactive agent may be physically bound to the polymer and/or the coating by entrapping, imbedding or otherwise containing a bioactive agent within the polymer and/or the coating network structure. A bioactive agent may be chemically bound to the polymer and/or the coating by way of a chemical reaction wherein a bioactive agent is covalently or ionically bonded to the polymer and/or the coating. Thus, various techniques for associating a bioactive agent in or on the polymer and/or the coating are contemplated herein.

The bioactive agent is present in amount that induces ossification or fibrous tissue growth depending on the effect desired. The amount of bioactive agent included on uncoated and/or coated areas of the scaffold 40 will depend on a variety of factors including the nature of the bioactive agent, the osteoinductive potential of the bioactive agent, and the nature of the carrier material (e.g., the biocompatible material forming the scaffold 40 or the mineral coating on the scaffold 40). Investigations have shown that a 1-100 ng/ml concentration of BMP can induce osteogenesis; and in one example, the BMP in the present invention can be released from the scaffold 40 in a time frame that varies from 10-50 days. Therefore, without intending to limit the invention in any way, in the case of bone morphogenetic proteins, it is contemplated that in one example a concentration of about 10-5000 ng of bone morphogenetic protein per $cm^3$ of material would be suitable for inducing ossification between the adjacent bones or adjacent bone surfaces.

Various regions of the scaffold 40 can include the coatings and associated bioactive agent. For example, the plates 45, 51 that are secured to the opposed vertebrae can be coated with continuous coating or islands of the coating and a bioactive agent associated with the coating so that bone growth is induced, while interior sections of the scaffold may not include coatings and may include different associated bioactive agents in order to promote growth of fibrous tissue. As an exemplary illustration, plates 45, 51 in FIG. 4 could include a continuous mineral coating and associated bioactive agent so that bone fixation to the adjacent vertebra is induced, while the wavy fibered microstructure 32 may include undifferentiated chondrocyte precursor cells from periosteum, mesenchymal stem cells from bone marrow, chondrocytes, sclerosing agents, angiogenesis activators, and/or angiogenesis inhibitors so fibrous growth is promoted in this region.

Preferably, the bioactive agents (e.g., bone morphogenetic proteins, chondrocytes) are associated with uncoated biocompatible material forming the scaffold 40 and/or the mineral coated portions of the scaffold 40 prior to inserting the wavy fibered microstructure 32 in the intervertebral disc space. For example, a bone morphogenetic protein may be chemically bonded (e.g., ionically or covalently bonded) to a calcium phosphate coating at a manufacturing site, or alternatively a bone morphogenetic protein may be chemically bonded to the calcium phosphate coating by a surgeon before and/or after implantation. The surgeon can reconstitute powdered bone morphogenetic protein with sterile water and apply the reconstituted powdered bone morphogenetic protein to the scaffold 40. Likewise, chondrocytes could be bonded to the wavy fibered microstructure 32 by a surgeon, or at the manufacturing site.

Figure 5A:
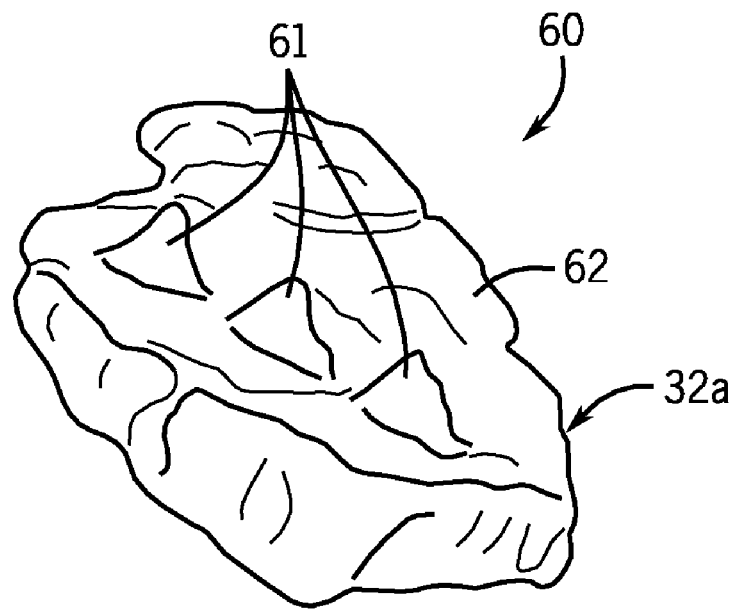
FIG. 5A shows an example of a spiked vertebrae interface on the top of an intervertebral disc scaffold.
Figure 5B:
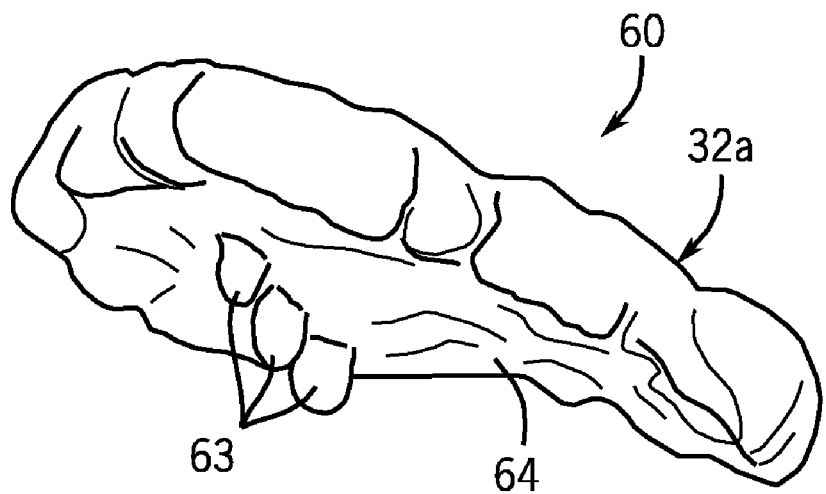
FIG. 5B shows an example of a spiked vertebrae interface on the bottom of the intervertebral disc scaffold of FIG. 5A.

Alternatively, fixation to the first upper vertebra and the adjacent second lower vertebra can be created as a keel riser structure, as shown in FIGS. 5A and 5B. The scaffold 60 of FIGS. 5A and 5B includes a wavy fibered microstructure 32a having top projections 61 from a top surface 62 of the scaffold 60 and bottom projections 63 from a bottom surface of the scaffold 60. When used in intervertebral disc repair, the wavy fibered microstructure 32a of the scaffold 60 would be positioned in the intervertebral space created by removal of the intervertebral disc between adjacent vertebrae. The top projections 61 would assist attachment to a bottom surface of the first upper vertebra, and the bottom projections 63 would assist attachment to the top surface an adjacent second lower vertebra.

The fixation structures, the attached plate structure and/or keel structure, will be porous polymers, ceramics and metals that may be made as composites with the actual disk scaffolding. The final scaffolding structure will be created by Boolean intersection of the fixation structures image design database with the scaffolding structure image design database. The final result will be a designed, porous scaffolding structure that forms a composite with the designed, porous fixation structures, as shown in FIG. 4 or FIGS. 5A and 5B.

Figure 6:
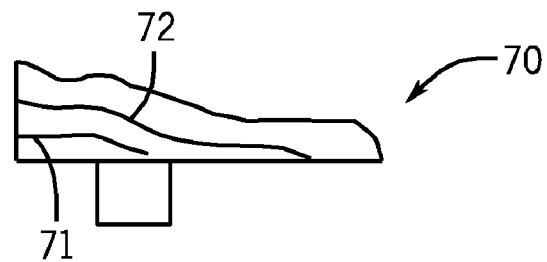
FIG. 6 shows a density map for a tibial plateau.
Figure 7:
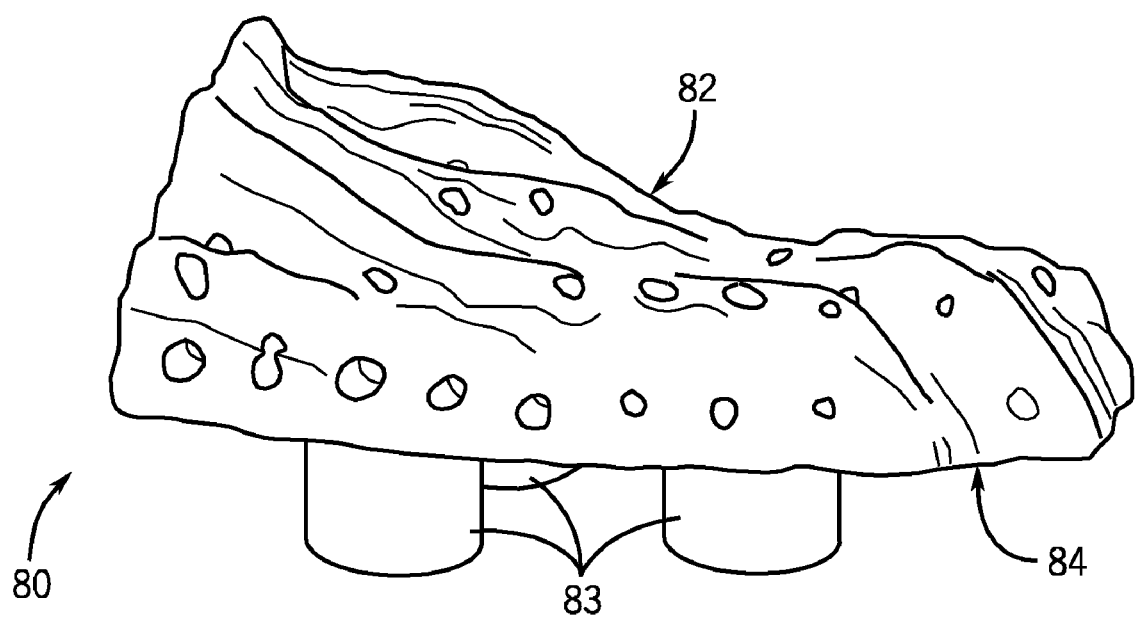
FIG. 7 shows an example final osteochondral scaffold with desired shape and microstructure.
Figure 8:
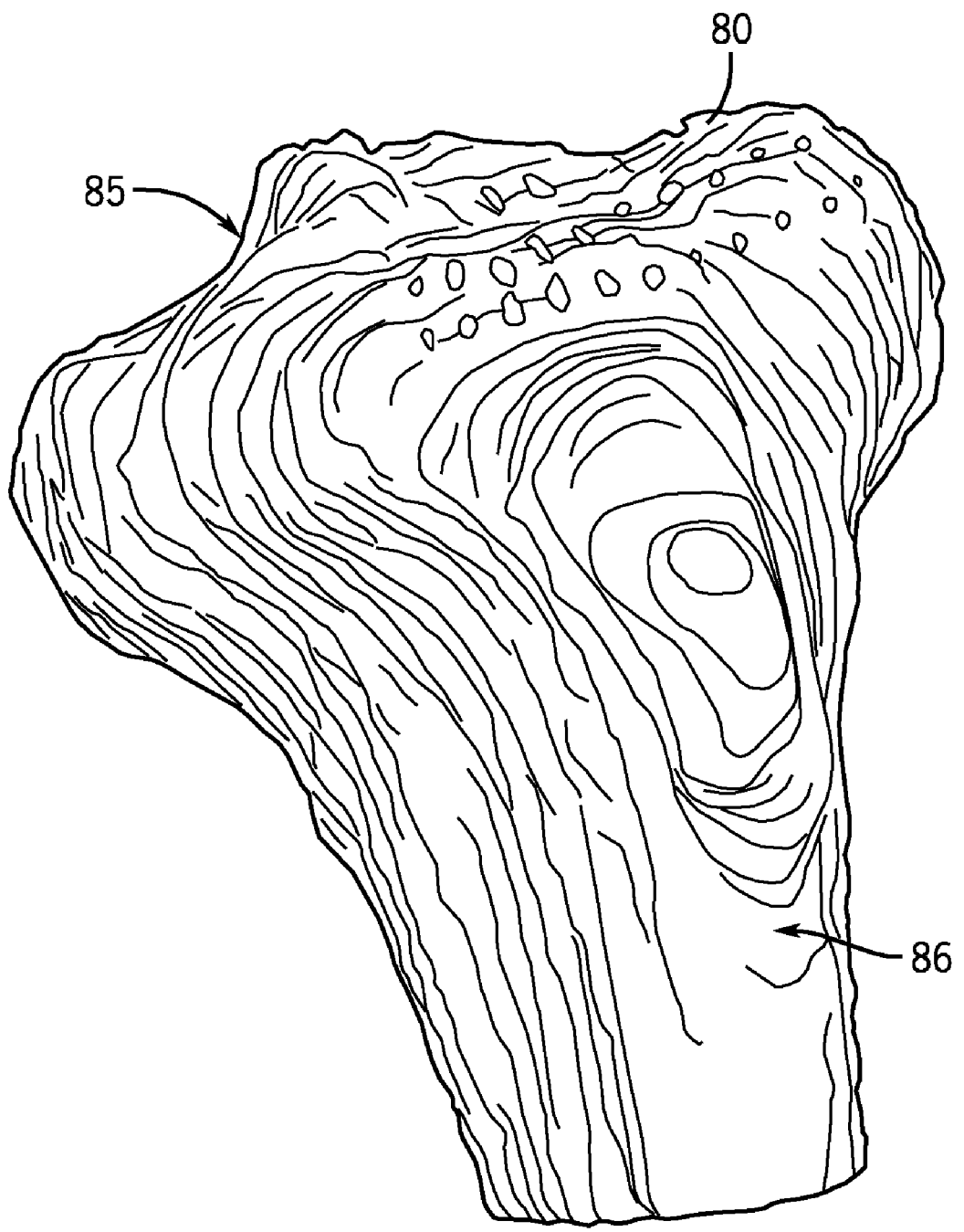
FIG. 8 shows the fit of a designed osteochondral scaffold into the whole tibia.

For the osteochondral scaffolding, the same fixation design procedure is used. FIG. 6 shows a density map 70 for the tibial plateau where lines 71, 72 mark the different density regions for mapping heterogeneous microstructure. In this case, microstructures similar to those designs in FIGS. 2A, 2B and 2C, including but not limited to the wavy fiber design 32 may be used to create functionally graded structures for the osteochondral scaffold. These designs are then substituted into density map 70 of FIG. 6 to create a scaffold design with desired shape and microstructure, along with fixation pegs. FIG. 7 shows an example final osteochondral scaffold 80 with desired shape and microstructure. The scaffold 80 includes a tibial plateau 82 having fixation pegs 83 extending downward from a bottom surface 84 of the scaffold 80. Preferably, the tibial plateau 82 region is designed to include spherical or elliptical pores in order to enhance cartilage growth. Also, the tibial plateau 82 region may be designed to have a lower elasticity than the pegs 83 to promote cartilage growth. The final fit of the osteochondral scaffold 80 in the tibial plateau 85 of a tibia 86 is shown in FIG. 8.

The scaffold 80 can comprise a porous biocompatible and biodegradable (if desired) porous material selected from polymeric materials, metallic materials, ceramic materials and mixtures thereof. In one example embodiment, the scaffold 80 is formed from polycaprolactone, a biocompatible and biodegradable polymer. However, other polymers such as polylactide, polyglycolide, poly(lactide-glycolide), poly(propylene fumarate), poly(caprolactone fumarate), polyethylene glycol, and poly(glycolide-co-caprolactone) may be advantageous for forming the scaffold 80.

An osteoconductive mineral coating can formed on at least a portion of the scaffold 80 where bone growth is desired. Bioactive agents would also be beneficial in the scaffold 80 of FIG. 7. For example, a bone morphogenetic protein may be chemically bonded (e.g., ionically or covalently bonded) to a calcium phosphate coating at the bottom surface 84 of the scaffold 80 for fixation to the tibia 86, while chondrocytes could be bonded to the tibial plateau 82 for cartilage growth.

Figure 9:
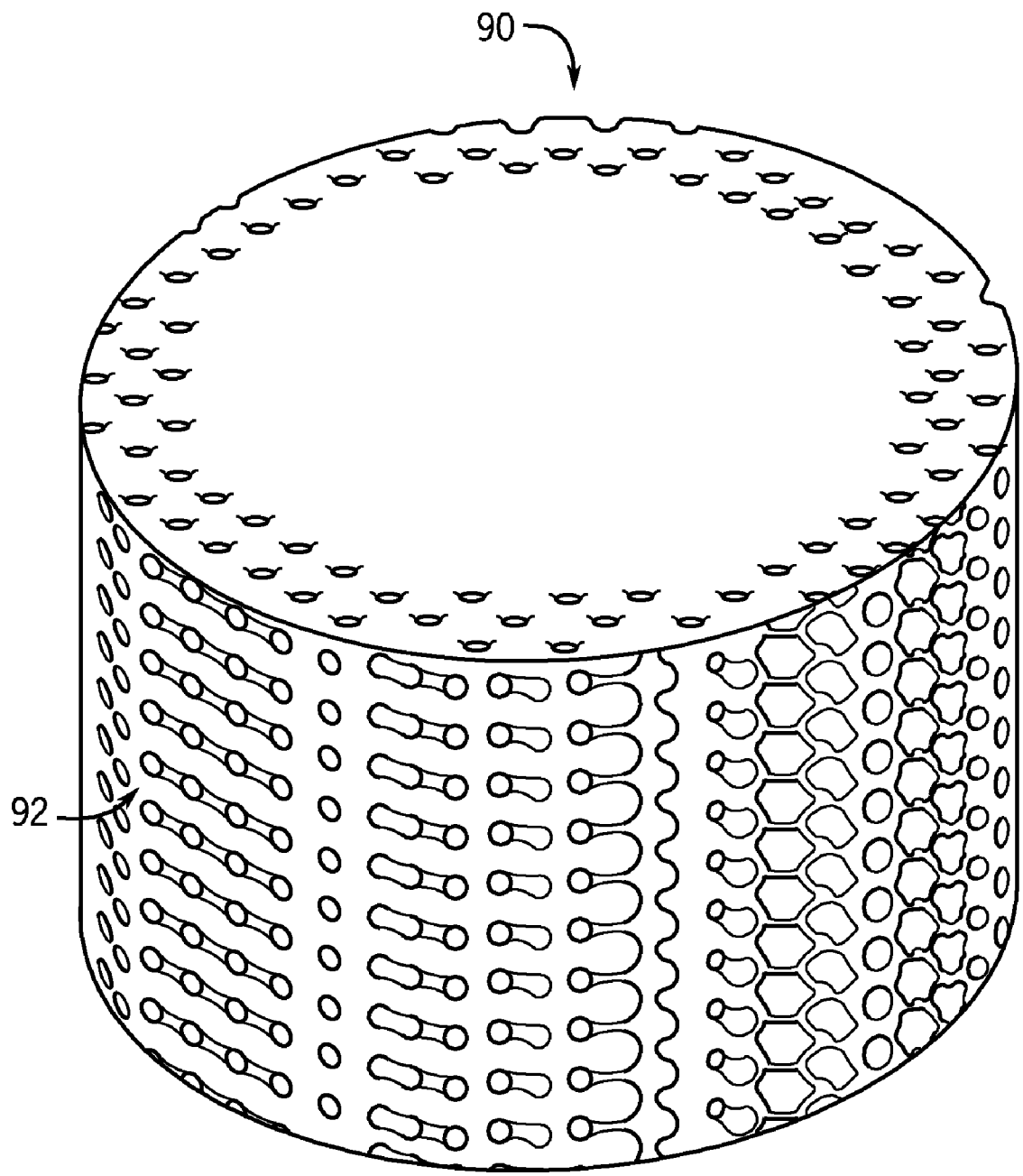
FIG. 9 shows a stem simulating a hip stem with a designed microstructure as an interface for fixation of the stem to surrounding bone.

In addition to being used for porous osteochondral scaffolds, the current designed microstructures could be used as bone interfaces for more traditional total joint replacements. In this case, a porous microstructure designed to have desired mechanical and mass transport properties would be designed to cover a joint replacement surface. The joint structure could be scanned using CT methods and the designed microstructure would be combined using Boolean methods. FIG. 9 shows such a combination for a simple solid stem 90 with a designed coating microstructure 92. The stem simulates a hip stem with a designed microstructure as an interface for fixation of the stem to surrounding bone.

If it is desired to create a scaffolding to engineer a new intervertebral disc, then the fabrication materials may include a composite of a degradable polymer for the structural scaffolding and a hydrogel interspersed within the designed scaffolding. A bioactive agent may also be included in the scaffolding. The degradable polymer may include one of the following, but is not limited to: (1) Polycaprolactone; (2) Polylactic Acid; (3) Polylactic-Polyglycolic Acid Co-polymer; (4) Polypropylene Fumarate; (5) Poly(glycerol-sebacate), and (6) Poly Octane Diol Citrate. The hydrogel may include, but is not limited to: (1) Fibrin Gel; (2) Polyethylene Glycol (PEG); (3) Collagen I Gel; and (4) Collagen/Hyaluronic Acid Gel.

If it is desired to create an intervertebral fusion device, then the scaffolding material may, in addition to the degradable polymers listed above, may also include, but is not limited to, the following: (1) Calcium Phosphate Ceramic; (2) Calcium Phosphate Ceramic/Polymer Composite; and (3) Titanium.

For an osteochondral scaffold, similar materials may be used to engineer the cartilage component including: (1) Polycaprolactone; (2) Polylactic Acid; (3) Polylactic-Polyglycolic Acid Co-polymer; (4) Polypropylene Fumarate, (5) poly (glycerol-sebacate), and (6) Poly Octane Diol Citrate. The hydrogel may include, but is not limited to: (1) Fibrin Gel; (2) Polyethylene Glycol (PEG); (3) Collagen I Gel; and (4) Collagen/Hyaluronic Acid Gel.

For the bone portion of the osteochondral scaffold, the materials may include polymer, ceramics or metals. Polymers may include, but are not limited to: (1) Polycaprolactone; (2) Polylactic Acid; (3) Polylactic-Polyglycolic Acid Co-polymer; and (4) Polypropylene Fumarate. These polymers may be surface engineered to include a biomineralized surface layer to improve osteoconductivity using a technique such as that described in U.S. Pat. No. 6,767,928, which is incorporated herein by reference as if fully set forth herein. In addition, both ceramics and metals may be used to fabricate the bone portion, including but not limited to: (1) Calcium Phosphate Ceramic; (2) Calcium Phosphate Ceramic/Polymer Composite; and (3) Titanium. The osteochondral scaffold may also include a bioactive agent in the bone and/or cartilage portion.

For the total joint replacement with a designed microstructure interface, the materials may be those commonly used for joint replacements including but not limited to: (1) Titanium Alloys such as Ti6Al4V; (2) Chrome Cobalt Molybdenum Alloys; and (3) Stainless Steel. The joint replacement may also include a bioactive agent.

The invention may be used for biologic regeneration of an intervertebral disc. Current attempts to resume partial or even full disc functions include disc regeneration by applying the state-of-art tissue engineering strategies. One key principle to conduct such strategies is to generate two distinct anatomic regions on the designed scaffolds that make up the intervertebral disc (IVD) and culture corresponding parenchymal cells at the central region resembling nucleus pulposus (NP) and the peripheral region for annulus fibrosus (AF). However, the concept has been only tested subcutaneously in a few studies. If the approach would be applied in situ, one can imagine there will be inevitably critical hurdles that can hinder any successfulness of full functional disc regeneration. The major concern of engineering full functional disc is cell survival. It is known that disc tissue is avascular with very low cellular density only 1% to 2% of the tissue volume. IVD cells, especially NP cells, rely highly on the nutrient supply diffused through the cartilaginous endplates on the superior and inferior surfaces. When a discectomy is executed, the endplates are exposed, and the insertion of the scaffold may interfere with the endplates due to the non-physical contact. In addition, the interface between the scaffold and the endplates may not be able to become fully integrated during neo-disc tissue formation. The situation will endanger the implanted cells by starving them away from the diffused nutrition and may result in significant cell death and fail the full disc regeneration.

As the alternative, the present invention proposes unified fibrous tissue regeneration for disc replacement. Originated from the clinical investigation, it is well known that some cases of interbody fusion can develop into asymptomatic pseudarthrosis, which indicates a non-solid, fibrous union rather than solid bone fusion. The reason physicians tend to explain for this phenomenon is that it may be because sufficient amount of fibrous tissue formation occurs intervertebrally and it provides sufficient stiffness to maintain the disc height, while preserving certain amount of motion without disturbing nerve roots. Moreover, it is speculated that with the formation of fibrous union, contact stress from body weight becomes more evenly distributed on the new fibrous construct, which, very possibly, reduces the etiology of axial discogenic pain.

By applying the approach already described on engineering scaffolds, the present invention can design a scaffold with the same inherent disc tissue properties to provide immediate support post-operatively. As it has been proven that sclerosing agents induce scarring for fibrosis and tissue contraction, the present invention combines these agents to increase fibrous tissue union in a controlled manner to confine the new fibrous tissue within the designed architecture. Any therapeutic proteins, growth factors, progenitor cells, and molecules/compounds, if aiming at beneficiating fibrous tissue formation, can be also included in our designed scaffold. Vehicles in gel forms or microspheres may also be associated with the usage of this invention as substantial components for applying the proposed unified fibrous tissue regeneration for disc replacement.

Once the intervertebral scaffolding image-design dataset is created, it can be automatically converted into a surface representation in .stl file format (stereolithography triangular facet data). This makes it possible to fabricate the intervertebral scaffolding from any type of Solid Free-Form Fabrication (SFF) system using either direct or indirect methods. The direct SFF methods include, but are not limited to: (1) Selective Laser Sintering (SLS); (2) Stereolithography (SLA); (3) Fused Deposition Modeling (FDM); and (4) Selective Laser Melting (SLM). One example solid freeform fabrication method may be found in U.S. Patent Application Publication No. 2003/0074096, which is incorporated herein by reference as if fully set forth herein.

Indirect methods are based on casting biomaterials, such as those listed above, into a mold created on a SFF system. In addition to the above SFF systems, the molds may also be created on direct 3D printing systems, including those systems that print wax. The indirect methods described in U.S. Patent Application Publication No. 2003/0006534 and U.S. Pat. No. 7,087,200 (which are both incorporated herein by reference as if fully set forth herein) may be used to make the disc scaffold.

Figure 10:
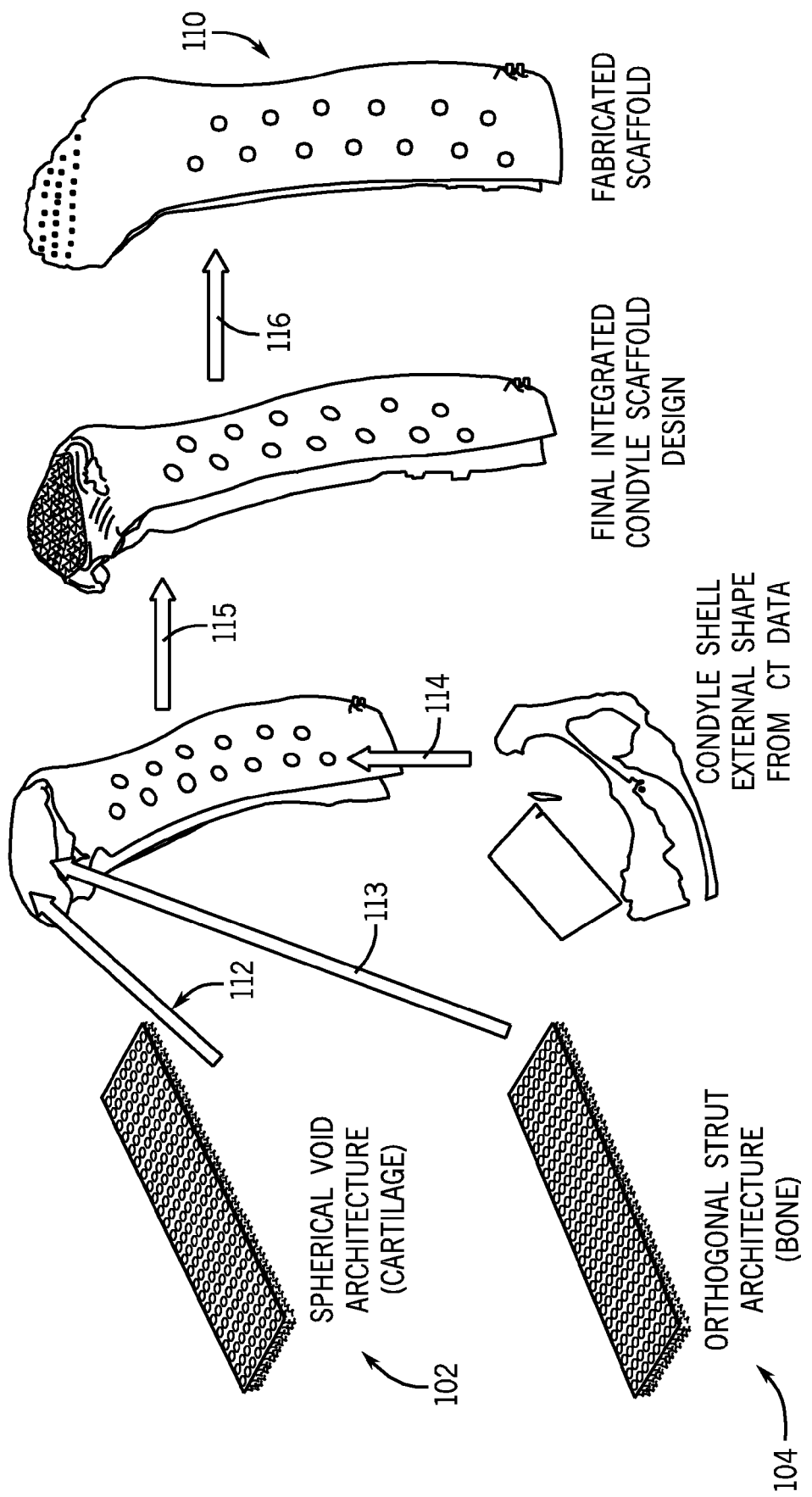
FIG. 10 shows the steps in engineering a mandibular condyle scaffold from image to fabricated scaffold.

The methodology of the invention has been implemented to make scaffolds for temporomandibular joint repair in a Yucatan Minipig model. The design procedure involved taking a CT scan of the minipig, using image-based techniques to design and fabricate the scaffold, and surgically implanting the scaffold. FIG. 10 shows the steps of an example procedure for mandibular condyle engineering from image to fabricated scaffold. Note that this scaffold has features created uniquely from image-based design, including a wrap-around ramus collar that allows surgical fixation, as shown with the screw holes.

Referring to FIG. 10, a spherical void architecture design 102 is chosen for the cartilage (surface) region of the image based design. An orthogonal strut architecture design 104 is chosen for the bone region of the image based design. The microstructure designs 102, 104 may be created using the image based design methods described in U.S. Patent Application Publication No. 2003/0069718. The resulting CT scan images provide the condyle shell anatomic external shape and design space for the scaffold 110. These images are stored as density distribution within a voxel dataset. The method merges the anatomic and architecture databases (see arrows 112, 113, 114). The method converts the voxel design to a surface or wire frame geometry (see arrow 115). The method fabricates the design scaffold from biomaterial using direct or indirect (casting) solid free form techniques (see arrow 116).

In addition, working prototypes have been built of a cervical disc design with anterior fixation plate and designed microstructure. See FIG. 11. The scaffold 120 of FIG. 11 includes the wavy fibered microstructure 32 in the correct anatomic shape for a natural intervertebral disc. A top fixation plate 125 includes spaced apart fastener holes 146a, (second hole not shown), and a top central U-shaped cutaway section 147. A bottom fixation plate 151 includes spaced apart fastener holes 152a, 152b, and a bottom central inverted U-shaped cutaway section 153. The wavy fibered microstructure 32 is integral with the fixation plates 125, 151. When used in intervertebral disc repair, the wavy fibered microstructure 32 of the scaffold 120 would be positioned in the intervertebral space created by removal of the intervertebral disc between adjacent vertebrae. Fasteners would be inserted in fastener holes 146a, (second hole not shown), for anterior attachment to a first upper vertebra, and fasteners would be inserted in fastener holes 152a, 152b for anterior attachment to an adjacent second lower vertebra. The top end surface 154 of the wavy fibered microstructure 32 would contact a lower surface of the first upper vertebra, and the opposite bottom end surface 155 of the wavy fibered microstructure 32 would contact an upper surface of the second lower vertebra. The wavy fibered microstructure 32 thereby provides mechanical load bearing support between the first upper vertebra and the second lower vertebra. The plates 125, 151 may include throughholes to allow fluid into the interior spaces of the scaffold to minimize any problems associated with tissue blockage of fluid. Optionally, flaps (not shown) can be provided on the plates 125, 151 to prevent backing out of the fasteners (e.g., fixation screws). In one embodiment, the fixation screws can be formed using the same biocompatible and biodegradable material with an osteoconductive mineral coating, and a bioactive agent associated with the biodegradable material and/or the coating.

The scaffold 120 can comprise a porous biocompatible and biodegradable (if desired) porous material selected from polymeric materials, metallic materials, ceramic materials and mixtures thereof. In one example embodiment, the scaffold 120 is formed from polycaprolactone, a biocompatible and biodegradable polymer. However, other polymers such as polylactide, polyglycolide, poly(lactide-glycolide), poly(propylene fumarate), poly(caprolactone fumarate), polyethylene glycol, and poly(glycolide-co-caprolactone) may be advantageous for forming the scaffold 120.

Figure 11:
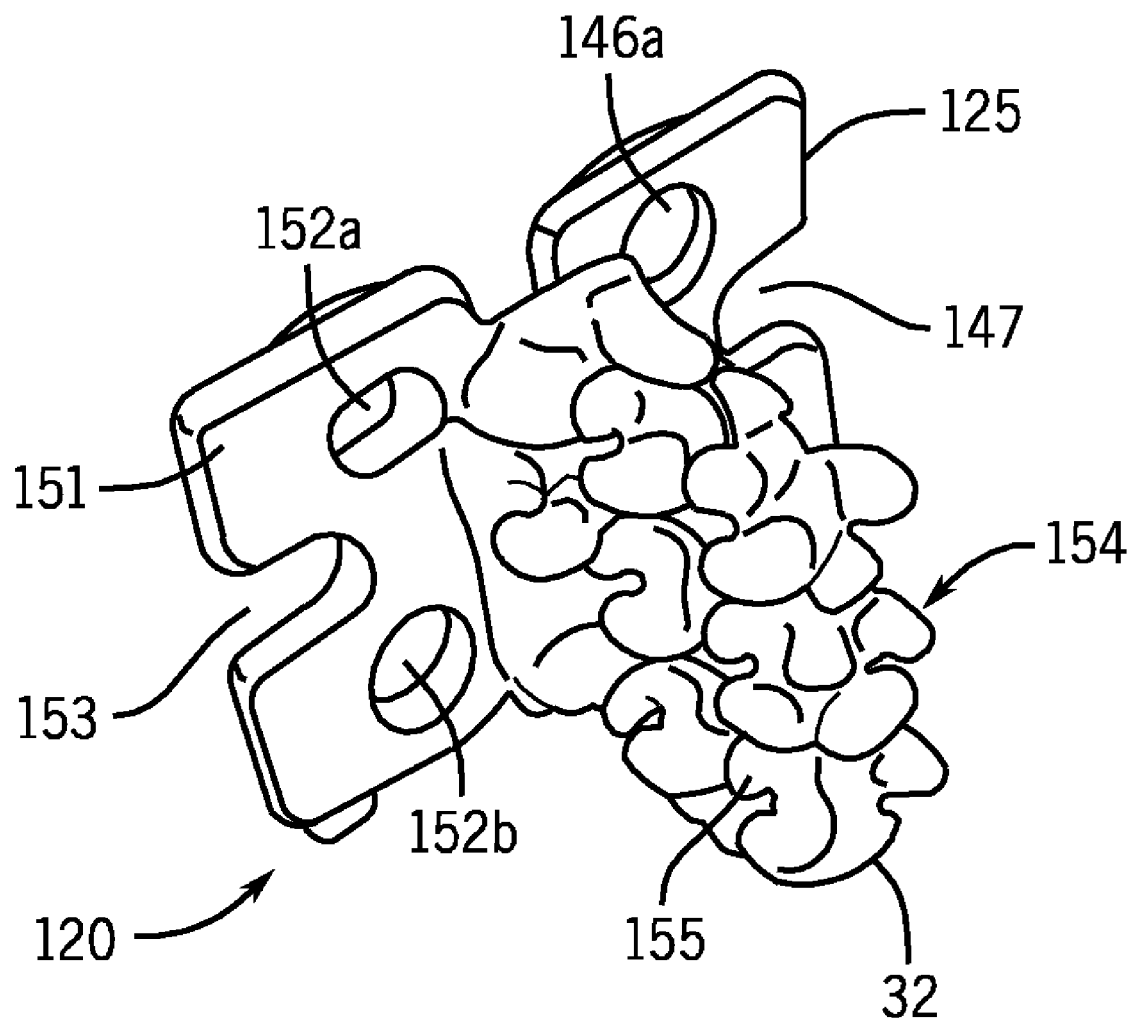
FIG. 11 shows an example of a cervical disc regeneration scaffold with designed anterior fixation plate and wavy fiber microstructure fabricated from polycaprolactone (PCL).

The vertical dimensions of the wavy fibered microstructure 32 in FIG. 11 can be adjusted accordingly for various different intervertebral distances. Likewise, the horizontal length of the fixation plates 125, 151 and their spatial relationship can be varied to ensure proper location of the fastener holes 146a, (second hole not shown), 152a, 152b adjacent the first upper vertebra and the second lower vertebra for securing the scaffold 120 to the first upper vertebra and the second lower vertebra. By varying the dimensions of the wavy fibered microstructure 32 and the fixation plates 125, 151 different size scaffolds 120 can be provided for selection by a surgeon.

This disc scaffold 120 also has features created uniquely from image-based design, including plates 125, 151 that allow surgical fixation, as shown with the fastener holes. Various regions of the disc scaffold 120 can include the mineral coatings and associated bioactive agent. For example, top and bottom end regions that are positioned near the opposed vertebrae can be coated with continuous or islands of the coating and associated bioactive agent so that bone growth is induced, while interior sections of the disc may not include coatings and associated bioactive agent in order to promote growth of fibrous tissue.

Because placement of the disc scaffold 120 of FIG. 11 may be performed using a medical imaging device and techniques (e.g., fluoroscopic observation), the disc scaffold 120 may further include at least one marking including a tracer that provides enhanced visibility via the medical imaging device. For example, non-limiting examples of radiopaque materials for enhanced visibility during fluoroscopy include barium sulfate, tungsten, tantalum, zirconium, platinum, gold, silver, stainless steel, titanium, alloys thereof, and mixtures thereof. Radiopaque markings can be used as an alignment aid in verifying the proper positioning of the disc scaffold. Also, the scaffold 120 may include a region of no material or radiolucent material such that the region forms an imaging window for enhanced visibility through the imaging window via a medical imaging device.

Therefore, it can be seen that the invention provides a method of designing an intervertebral body scaffolding with controlled elastic and permeability properties that may mimic that natural function of vertebral discs. The designed permeability will allow nutrients to diffuse into the disc to allow survival of delivered cells or cells that migrate into the disc. Disc scaffolding permeability could also be designed to mimic the permeability distribution of normal discs. In addition, with the wavy fibered microstructure, the disc scaffold could exhibit nonlinear behavior similar to human intervertebral disc. This capability is not seen in prior artificial discs, tissue engineered discs, or spine fusion approaches. Furthermore, the disc may be fabricated as a composite material.

The invention also provides a method of designing an osteochondral scaffold design with a joint interface design. The invention includes the ability to design effective mechanical and mass transport properties of the interface and the ability to fabricate these controlled microstructures. In addition, invention includes the ability to readily fabricate adjunct surgical fixation based on anatomic features.

The invention also provides a method of designing a joint replacement. The invention provides methods and devices that stabilize a joint, promote fibrous tissue union of adjacent bones, and allow for motion between adjacent bones.

Although the invention has been described in considerable detail with reference to certain embodiments, one skilled in the art will appreciate that the present invention can be practiced by other than the described embodiments, which have been presented for purposes of illustration and not of limitation. In particular, the methods and devices described herein can used to promote fibrous union between any bone surfaces. Therefore, the scope of the appended claims should not be limited to the description of the embodiments contained herein.

What is claimed is:

1. A method, implemented on a computer having at least a processor and storage, for designing a tissue scaffold for generating tissue in a patient, the method comprising:
   creating a first set of databases representing a plurality of porous microstructure designs for the scaffold in image based format;
   creating a second database representing scaffold exterior geometry desired to replace the native tissue in the patient in image based format;
   creating a third database representing a plurality of scaffold external fixation structures for attaching the scaffold to existing patient tissue;
   and merging the first set of databases representing the desired microstructure designs with the second database and the third database into an image-based design of the scaffold.

2. The method of claim 1 further comprising:
converting the image-based design to a fabrication geometry.

3. The method of claim 1 wherein:
the scaffold external fixation structure is designed to comprise at least one projection extending away from the scaffold.

4. The method of claim 3 wherein:
the projection is a peg or a spike or a plate.

5. The method of claim 1 wherein:
the scaffold is designed for intervertebral disc repair, or articulating joint repair, or total joint replacement.

6. The method of claim 1 wherein the scaffold external fixation structure for attaching the scaffold to existing patient tissue is created using the first set of databases representing the plurality of porous microstructure designs.

7. The method of claim 1 wherein the scaffold external fixation structure for attaching the scaffold to existing patient tissue is porous.

8. The method of claim 1 wherein the tissue is an intervertebral disc.

9. A method implemented on a computer having at least a processor and storage, for designing an intervertebral disc scaffold, the method comprising:
creating a first set of databases representing a plurality of porous microstructure designs for the scaffold in image based format including one or more regions designed to have biochemical properties or to include bioactive agents;
creating a second database representing scaffold exterior geometry desired to replace the native disc in the patient in image based format;
and merging the first set of databases representing the desired microstructure designs with the second database into an image-based design of the scaffold, and
wherein the image-based design includes a region designed to have a first biochemical property.

10. The method of claim 9 further comprising:
converting the image-based design to a fabrication geometry.

11. The method of claim 9 wherein:
the image-based design of the scaffold includes an outer annulus having a first designed porous microstructure, and
the image-based design of the scaffold includes a central region having a second designed microstructure.

12. The method of claim 9 wherein:
at least one of the microstructure designs is a wavy fiber design.

13. The method of claim 9 wherein:
the image-based design of the scaffold is designed to include spherical or elliptical pores.

14. The method of claim 9 wherein the region designed to have a first biochemical property comprises a polymer containing a bioactive agent.

15. A method implemented on a computer having at least a processor and storage, for designing an osteochondral scaffold for replacing native tissue in a patient, the method comprising:
creating a first set of databases representing a plurality of porous microstructure designs for the scaffold in image based format including one or more regions designed to have biochemical properties or to include bioactive agents;
creating a second database representing scaffold exterior geometry desired to replace the native tissue in the patient in image based format; and
merging the first set of databases representing the desired microstructure designs with the second database into an image-based design of the scaffold,
wherein the image-based design includes a bone region designed to have a first biochemical property and a cartilage region designed to have a second biochemical property.

16. The method of claim 15 wherein:
the first biochemical property is a mass transport property, and the second biochemical property is a mass transport property.

17. The method of claim 15 wherein:
the first biochemical property is achieved by coating at least a portion of the bone region with an osteoconductive mineral comprising a calcium compound.

18. The method of claim 15, wherein the bone region designed to have a first biochemical property comprises a polymer containing a bioactive agent.

19. A method implemented on a computer having at least a processor and storage, for designing a joint replacement for a patient, the method comprising:
creating a first set of databases representing a plurality of porous microstructure designs for the joint replacement in image based format including one or more regions designed to have biochemical properties or to include bioactive agents;
creating a second database representing joint replacement exterior geometry in image based format; and
merging the first set of databases representing the desired microstructure designs with the second database into an image-based design of the joint replacement,
wherein the image-based design includes a bone region designed to have a first biochemical property and a surface region designed to have a second biochemical property.

20. The method of claim 19 wherein:
the first biochemical property is a mass transport property, and
the second biochemical property is a mass transport property.

21. The method of claim 19 wherein:
the first biochemical property is achieved by coating at least a portion of the bone region with an osteoconductive mineral comprising a calcium compound.

22. The method of claim 19 wherein the bone region designed to have a first biochemical property comprises a polymer containing a bioactive agent.

* * * * *